United States Patent [19]

Geisberger et al.

[11] Patent Number: 5,252,768

[45] Date of Patent: Oct. 12, 1993

[54] PROCESS FOR PREPARING A DIMETHYLCHLOROSILANE

[75] Inventors: Gilbert Geisberger, Altoetting; Bernd Pachaly, Burghausen, both of Fed. Rep. of Germany

[73] Assignee: Wacker-Chemie GmbH, Munich, Fed. Rep. of Germany

[21] Appl. No.: 23,449

[22] Filed: Feb. 25, 1993

[30] Foreign Application Priority Data

Mar. 13, 1992 [DE] Fed. Rep. of Germany ....... 4208152

[51] Int. Cl.$^5$ .................................................. C07F 7/08
[52] U.S. Cl. ..................................................... 556/469
[58] Field of Search ............................................ 556/469

[56] References Cited

U.S. PATENT DOCUMENTS

| | | | |
|---|---|---|---|
| 2,732,282 | 1/1956 | Bailey et al. | 556/469 X |
| 2,834,648 | 5/1958 | Bailey et al. | 556/469 X |
| 3,399,222 | 8/1968 | Weyenberg | 556/469 |
| 4,605,543 | 8/1986 | Lepage et al. | 556/469 X |
| 4,667,048 | 5/1987 | Inoue et al. | 556/469 |
| 4,746,752 | 5/1988 | Lepage et al. | 556/469 |
| 4,870,200 | 9/1989 | Ottlinger et al. | 556/469 |

OTHER PUBLICATIONS

K. Moedritzer et al., Journal of Organometallic Chemistry 12 (1968) pp. 69–77.

K. G. Allum et al., Journal of Organometallic Chemistry 87 (1975), p. 203.

E. L. Zichy, Journal of Organometallic Chemistry 4 (1965), pp. 411–412.

W. Noll, Chemie und Technologie der Silicone, Verlag Chemie, Weinheim, 2. Auflage (1968), pp. 76–77.

W. Noll, Chemistry and Technology of Silicones, Academic Press, (1968), pp. 87–88.

*Primary Examiner*—Paul F. Shaver

[57] ABSTRACT

A process for the preparation of dimethylchlorosilane by the redistribution reaction of dimethyldichlorosilane with at least one silane having Si-bonded methyl groups, hydrogen atoms and/or chlorine atoms in the presence of a catalyst, in which the silane is methylchlorosilane and/or methylsilane and the catalyst is a support which is insoluble in the reaction medium and to which $NR_2R^1$ groups or $\ominus X \oplus NR_3R^1$ groups are covalently bonded, in which R is the same or different and represents a hydrogen atom or a monovalent hydrocarbon radical having from 1 to 20 carbon atoms per radical, or two R radicals together represent a divalent hydrocarbon radical having from 4 to 11 carbon atoms, which is optionally interrupted by a hetero atom, $R^1$ represents a divalent hydrocarbon radical having from 1 to 20 carbon atoms per radical and $X\ominus$ represents a chloride ion, bromide ion or iodide ion.

2 Claims, 2 Drawing Sheets

PROCESS FOR PREPARING A DIMETHYLCHLOROSILANE

The invention relates to a process for the preparation of dimethylchlorosilane by the redistribution reaction. More particularly, the process relates to the preparation of dimethylchlorosilane by the rearrangement of dimethyldichlorosilane with at least one silane having Si-bonded methyl groups, hydrogen atoms and/or chlorine atoms in the presence of a catalyst.

BACKGROUND OF THE INVENTION

In the so-called direct synthesis reaction, a process in which silicon powder is reacted with methyl chloride in the presence of a copper catalyst, other silanes are obtained in addition to the main product dimethyldichlorosilane. For example, dimethylchlorosilane is obtained, but only in low yields.

The redistribution of two silanes having Si-bonded methyl groups, hydrogen atoms and/or chlorine atoms in the presence of quaternary ammonium salts is disclosed in K. Moedritzer et al., Journal of Organometallic Chemistry 12 (1968) 69–77.

According to U.S. Pat. No. 3,399,222 (issued Aug. 27, 1968, D. R. Weyenberg et al., Dow Corning Corp.), in the redistribution reaction of dimethyldichlorosilane with methyldichlorosilane in the presence of quaternary ammonium salts, the following equilibrium is on the left hand side:

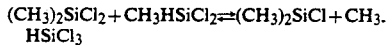

$(CH_3)_2SiCl_2 + CH_3HSiCl_2 \rightleftharpoons (CH_3)_2SiCl + CH_3HSiCl_3$

In U.S. 4,870,200 (issued Sep. 26, 1989, R. Ottlinger et al., Wacker-Chemie GmbH) the disproportionation of methyldichlorosilane to form methylchlorosilane and/or methylsilane in the presence of a catalyst, composed of a support which is insoluble in the reaction medium and to which tertiary, amine groups or quaternary ammonium groups are covalently bonded, is described.

It is an object of the present invention to provide a process for the preparation of dimethylchlorosilane by the redistribution reaction of dimethyldichlorosilane with at least one silane having Si-bonded methyl groups, hydrogen atoms and/or chlorine atoms in the presence of a catalyst. Another object of the present invention is to provide a process which produces good yields of dimethylchlorosilane. A further object of the present invention is to provide a process in which the redistribution reaction proceeds in the presence of heterogeneous catalysts. A further object of the present invention is to provide a process in which the catalyst can easily be removed from the reaction mixture and recovered. A still further object of the present invention is to provide a continuous process for preparing dimethylchlorosilane.

SUMMARY OF THE INVENTION

The foregoing objects and others which will become apparent from the following description are accomplished in accordance with this invention, generally speaking, by providing a process for the preparation of dimethylchlorosilane by the redistribution reaction of dimethyldichlorosilane with at least one silane having Si-bonded methyl groups, hydrogen atoms and/or chlorine atoms in the presence of a catalyst, in which the silane is methylchlorosilane and/or methylsilane and the catalyst is a support which is insoluble in the reaction medium and to which $NR_2R^1$ groups or $\ominus X \oplus NR_3R^1$ groups are covalently bonded, in which R is the same or different and represents a hydrogen atom or a monovalent hydrocarbon radical having from 1 to 20 carbon atoms per radical, or two R radicals together represent a divalent hydrocarbon radical having 4 to 11 carbon atoms, which is optionally interrupted by a hetero atom, $R^1$ represents a divalent hydrocarbon radical having from 1 to 20 carbon atoms per radical and $X^\ominus$ represents a chloride ion, bromide ion or iodide ion.

Description of the Invention

The process of this invention has the advantage that during the redistribution reaction Si-bonded chlorine atoms and hydrogen atoms are rearranged but no rearrangement of Si-bonded methyl groups occurs.

The methylchlorosilane and/or methylsilane preferably used are the disproportionation products of methyldichlorosilane which are obtained on disproportionation of methyldichlorosilane in the presence of a support which is insoluble in the reaction medium and to which $NR_2R^1$ groups or $\ominus X \oplus NR_3R^1$ groups are covalently bonded, where R, $R^1$ and $X^\ominus$ are the same as above.

Examples of radicals R are alkyl radicals, such as the methyl, ethyl, n-propyl, iso-propyl, n-butyl, iso-butyl, ter-butyl, n-pentyl, iso-pentyl, neo-pentyl or tert-pentyl radicals; hexyl radicals, such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical; tetradecyl radicals; hexadecyl radicals and octadecyl radicals, such as the n-octadecyl radical; cycloalkyl radicals, such as cyclopentyl, cyclohexyl or cycloheptyl radicals and methylcyclohexyl radicals; aryl radicals, such as the phenyl radical; alkaryl radicals, such as o-, m- and p-tolyl radicals; xylyl radicals and ethylphenyl radicals and aralkyl radicals, such as the benzyl radical and the α- and β-phenylethyl radical.

Examples of radicals in which the two R radicals together represent a divalent hydrocarbon radical are those of the formula $-(CH_2)_5-$ and $-(CH_2)_4-$.

Examples of radicals in which the two R radicals together represent a divalent hydrocarbon radical which is interrupted by a hetero atom are those of the formula $-(CH_2)_2-O-(CH_2)_2-$ and $-(CH_2)_2-O-(CH_2)_2-O-(CH_2)_2-$.

Preferred examples of R radicals are alkyl radicals, in which the methyl radical is particularly preferred because of its availability.

Examples of radicals $R^1$ are alkylene radicals, such as the methylene, ethylene, n-propylene, isopropylene, n-butylene, isobutylene, n-pentylene and isopentylene radicals; hexylene radicals, such as the n-hexylene radical; heptylene radicals, such as the n-heptylene radical; octylene radicals, such as the n-octylene radical and isooctylene radicals; nonylene radicals, such as the n-nonylene radical; decylene radicals, such as the n-decylene radical; dodecylene radicals, such as the n-dodecylene radical; tetradecylene radicals; hexadecylene radicals and octadecylene radicals, such as the n-octadecylene radical; cycloalkylene radicals, such as cyclopentylene, cyclohexylene and cycloheptylene radicals; arylene radicals, such as the phenylene radical; alkarylene radicals, such as tolylene radicals, and aralkylene radicals, such as the benzylene radical.

Preferred examples of $R^1$ radicals are alkylene radicals, in the n-propylene radical is particularly preferred.

The preferred halide ion $X^\ominus$ is the chloride ion.

Preferred supports which are insoluble in the reaction medium comprise substances having hydroxyl group's at the surface. Examples of such substances are acid clays, such as Tonsil, montmorillonite and other aluminosilicates in the $H^\oplus$ form, zeolites, porous glass, such as controlled pore glass, porous ceramics, such as controlled pore ceramics, porous silica, such as precipitated or pyrogenic silica, porous alumina and porous mullite.

Additional preferred examples of supports which are insoluble in the reaction medium are dried hydrolysis products of functional silanes or polystyrenes, such as polystyrene crosslinked with divinylbenzene.

Supports which are particularly preferred are porous silica or polystyrene crosslinked with divinylbenzene.

When the substances have hydroxyl groups at the surface, the covalent bonding of the $NR_2R^1$ of $\ominus X \oplus NR_3R^1$ groups to the support is preferably effected by reaction of these hydroxyl groups with the hydrolyzable groups Y of the compounds of formula

  (I)

in which Y represents a hydrolyzable group $R^2$ represents a monovalent hydrocarbon radical having from 1 to 12 carbon atoms per radical, n represents an integer of from 1 to 20, x represents 0 or 1 and Z represents a $NR_2$ or $\ominus X \oplus NR_3$ group, where R is the same as above, preferably in an inert solvent at temperatures in the range of from preferably 0° to 200° C.

Examples of hydrolyzable groups represented by Y are alkoxy radicals, such as the methoxy or ethoxy radical, and halogen atoms, such as the chlorine atom.

Examples of radicals $R^2$ are alkyl radicals, such as the methyl, ethyl, n-propyl, isopropyl, n-butyl or isobutyl radicals; aryl radicals, such as the phenyl radical; and alkaryl radicals, such o-, m- and p-tolyl radicals.

Because of its availability, it is preferred that the $R^2$ radical be a methyl radical and the preferred values for n are 2 or 3, that is, the ethylene or propylene radical.

Examples of preferred compounds of the formula

  (I)

are 3-aminopropyltrimethoxysilane, 3-aminopropyltriethoxysilane, 2-aminoethyltrimethoxysilane, 2-aminoethyltriethoxysilane and 3-aminopropyltrichlorosilane.

In particular, N,N-diethylaminopropyltrimethoxysilane, morpholinopropyltriethoxysilane, trimethoxysilyl-3-propyl-N,N,N-dimethyloctylammonium chloride and trimethoxysilyl-3-propyl-N,N,N-dimethyloctadecylammonium chloride are preferred.

Preferably from 5 to 30% by weight, and in particular from 10 to 20% by weight, of compounds of formula (I.), based on the weight of the untreated support, are used.

Preferably a 40 to 60% solution of the compound of formula (I) in an alcohol, such as methanol, based on the weight of the compound of formula (I), is used.

Examples of inert solvents are toluene, xylene and chlorobenzene.

The catalyst thus obtained on reaction is preferably filtered off and preferably dried at a temperature of from 50° to 100° C.

In the case of the dried hydrolysis products of functional silanes the covalent bonding of the $NR_2R^1$ groups or $\ominus X \oplus NR_3R^1$ groups to the support takes place during the preparation of the hydrolysis products, which can be prepared by known methods; cf. K. G. Allum et al., J. Organometal. Chem. 87, 203 (1975).

The functional silanes used are preferably compounds of formula (I), such as $(EtO)_3SiCH_2CH_2CH_2NEt_2$, $(MeO)_3SiCH_2CH_2CH_2NMe_2C_{18}H_{37}^\oplus Cl^\ominus$, $(MeO)_3SiCH_2CH_2CH_2NME_2C_{10}H_{21}^\oplus Cl^\ominus$ or $(MeO)_3SiCH_2CH_2CH_2NMe_3^\oplus Cl^\ominus$, where Me represents a methyl radical and an ethyl radical.

In order to modify the hydrolysis products, the hydrolysis can also be carried out in the presence of additional compounds, such as water glass, titanium halides or titanium alcoholates, zirconium halides or zirconium alcoholates, aluminum halides or aluminum alcoholates, silicon halides or silicon alcoholates, and tin halides or tin alcoholates.

Examples of compounds used in the preparation of the hydrolysis products are $Si(OEt)_4$ and $(EtO)_3SiCH_2CH_2CH_2NEt_2$; $Ti(OBu)_4$ and $(MeO)_3SiCH_2CH_2CH_2NMe_2C_{18}H_{37}^\oplus Cl^\ominus$; $Na_2SiO_3$ and $(MeO)_3SiCH_2CH_2CH_2NMe_2C_{10}H_{21}^\oplus Cl^\ominus$; $Al(O-i-Pr)_3$ and $(MeO)_3SiCH_2CH_2CH_2NMe_3^\oplus Cl^\ominus$, where Me represents a methyl radical, Et an ethyl radical, i-Pr an isopropyl radical and Bu a n-butyl radical.

Polystyrenes, such as, for example, polystyrene crosslinked with divinylbenzene, having covalently bonded $NR_2R^1$ groups or $\ominus X \oplus NR_3R^1$ groups are known as basic ion exchangers and are available commercially. Examples of preferred basic ion exchangers are Amberlite IRA 93 and Amberlyst A21 (both Rohm and Haas GmbH, Frankfurt, Germany) and Lewatit 35A, Lewatit MP64, Lewatit MP65, Lewatit MP62 (all Bayer AG, Leverkusen, Germany).

The supports having covalently bonded $NR_2R^1$ groups or $\ominus X \oplus NR_3R^1$ groups are preferably in the form of powders having an average particle size distribution of preferably from 1 μm to 1 mm, and more preferably from 0.5 to 1 mm, or have been converted, before or after covalent bonding of the $NR_2R^1$ groups or $\ominus X \oplus NR_3R^1$ groups to the support, in a manner known per se for example into moldings such as rings, half-rings, rods, spheres, cubes or saddles. Preferred moldings are in the form of rings, spheres or cubes.

The moldings are formed from finely divided catalysts having an average particle size distribution of from 1 μm to 1 mm, and if appropriate with the addition of organic or inorganic binders or under crosslinking hydrolysis. Shaping can be effected by means of pressing at an elevated temperature or by means of sintering under elevated pressure, but also by means of an extruder with subsequent comminution of the sections.

Examples of organic or inorganic binders are epoxy resins, water glass and organic polymers, such as polyethylene, polypropylene, polystyrene, polyvinyl chloride, polyacrylate and polyamide.

In order to increase the porosity of the shaped catalysts, a water-soluble substance, such as sodium chloride or sodium sulfate, is preferably added to the compositions prior to shaping, which substance is dissolved out after the shaping step and thus produces a highly active macroporosity.

Preferably, the methylchlorosilane and/or methylsilane used in the process of this invention is prepared by disproportionation of methyldichlorosilane in the presence of a catalyst. Examples of catalysts are tertiary amines and quaternary ammonium salts, such as tetrabutylammonium chloride.

Preferably, the methylchlorosilane and/or methylsilane used in the process of this invention is prepared by disproportionation of methyldichlorosilane, as described in U.S. Pat. No. 4,870,200.

Methyldichlorosilane is obtained from the so-called direct synthesis in addition to the main product dimethyldichlorosilane.

Methylchlorosilane and methylsilane can also be prepared by other processes.

The methylsilane used in the process of this invention can be prepared, for example, from methylhydrogenosiloxanes by the process described in E. L. Zicky, J. Organometal Chem 4, 411–412 (1965) or by hydrogenation of methylchlorosilanes with metal hydrides in accordance with W. Noll, Chemie und Technologie der Silicone (Silicone Chemistry and Technology), Verlag Chemie, Weinheim, 2nd edition, pages 76 to 77, 1968.

The process of this invention is carried out in a heterogeneous phase.

The educts of dimethyldichlorosilane and also methylchlorosilane and/or methylsilane are preferably used in gas form but can also be used in liquid form or in solution in an inert organic solvent, such as hexane, toluene, xylene or chlorobenzene.

When the reaction is conducted in the liquid phase, a suspension, composed of the finely divided catalyst and the educts of dimethyldichlorosilane and also methylchlorosilane and/or methylsilane, is heated at a temperature of preferably from 0° to 250° C. and pressure of preferably 0.1 to 20 bar and the resulting reaction mixture is separated by fractional distillation.

When the reaction is conducted in the gas phase, the solid catalyst, preferably in finely divided form, is used in a fixed bed or fluidized bed. If the solid catalyst is used in the form of moldings in a rectification column, the reaction can take place either in the gas phase or in the liquid phase.

In the case of the arrangement of the catalyst in a fixed bed or fluidized bed gaseous methylchlorosilane and/or methylsilane together with gaseous dimethyldichlorosilane are passed under a pressure of preferably 0.1 to 15 bar, more; preferably from 1 to 7 bar, and at a temperature of preferably from 0° to 300° C., and more preferably from 0° to 150° C., through a fixed bed or fluidized bed composed of finely divided catalyst. The resulting reaction mixture is then condensed and separated by fractional distillation and the dimethylchlorosilane is thus obtained. With this procedure, the methylsilane obtained as top product from the disproportionation of methyldichlorosilane in a rectification column, methylchlorosilane or a mixture of methylsilane and methylchlorosilane, as described in U.S. Pat. No. 4,870,200, is preferably used.

In the case of the arrangement of the catalyst in the form of moldings in a rectification column, methylchlorosilane and/or methylsilane are fed into the lower section and dimethyldichlorosilane is fed into the upper section of the rectification column under a pressure of preferably 0.1 to 20 bar, more preferably from 3 to 8 bar, and at a temperature of preferably from 0° to 250° C., and more preferably from 50° to 150° C. The reaction mixture obtained at the top of the column is then separated by fractional distillation.

The preferred embodiment of the process of this invention comprises carrying out both the dispropor-tionation of methyldichlorosilane and the redistribution in a rectification column filled with catalyst, so that no isolation or intermediate storage of the methylsilane and/or methylchlorosilane is necessary. The methyldichlorosilane is introduced into the lower section of the column. With this procedure the disproportionation takes place in the lower section of the column, preferably at a temperature of −10° to 250° C. at a pressure of 0.1 to 15 bar. The higher-boiling methyltrichlorosilane collects at the bottom, from where it is removed, and the low-boiling compounds methylchlorosilane and/or methylsilane, which tend to rise to the top of the column, rearrange with the gaseous dimethyldichlorosilane introduced into the upper section of the column, preferably at a temperature of from −10° to 250° C. and at a pressure of from 0.1 to 15 bar. The reaction products recovered from the top of the column are introduced into a second rectification column. The low-boiling compounds methylsilane, methylchlorosilane and dimethylsilane, which emerge from the top of the column in the second rectification column, are condensed and recycled into the first rectification column; the higher-boiling reaction products are removed from the bottom. The higher-boiling reaction products are separated by distillation and the dimethylchlorosilane is thus obtained.

The process of this invention can be carried out batchwise, semi-continuously or continuously. It is preferably carried out continuously.

Dimethylchlorosilane is a valuable starting compound for the preparation of functional silanes or siloxanes via the hydrosilylation of aliphatic organic compounds having a double or triple bond and for the preparation of organopolysiloxanes having dimethylhydrogenosilyl groups, which are used in silicone rubber compositions which crosslink by addition.

The methyltrichlorosilane obtained as by-product, mainly from the disproportionation of methyldichlorosilane, can also be utilized economically, for example for the preparation of methylsilicone resins and for the preparation of highly dispersed silica produced by flame hydrolysis.

Example 1

Preparation of the catalyst

A 50% solution of 3-trimethoxysilylpropyloctadecyldimethylammonium chloride in methanol was added to highly dispersed silica in the form of spheres 3 to 5 mm in diameter, KC-Siliperl AF 125 (Kali-Chemie, Hannover, Germany), and the mixture was boiled for several hours under toluene reflux. The solid was then filtered off from the solvents and the support, which was now functionalized, was dried at 100° C. under vacuum.

Examples 2 to 5

The catalyst prepared according to Example 1 was packed into a thermostatically controlled tube 2.4 cm in diameter to a packed height of 20 cm. The amounts and compositions of the silane passed through were varied (Examples 2–5) and the product compositions were determined by $^1$H NMR spectroscopy. The experimental conditions and results are summarized in the following table.

The MeSiH$_3$ used in Examples 2 to 4 was prepared in accordance with the process described in Example 3 of U.S. Pat. No. 4,870,200. The MeSiH$_2$Cl used in Example 5 was prepared in the following way.

A homogeneous solution of 90 g of tetrabutylammonium chloride in 1380 g of methyldichlorosilane was heated to boil in a 2 liter three-necked flask surmounted by a packed column, the column head cooled to −30° C., and a reflux divider. At a top temperature of 8° C. and a bottom temperature which rose during the reaction from 44° to 50° C., 150 g of methylchlorosilane were obtained in three hours as distillate in the receiver cooled to −30° C.

TABLE

|  | Examples | | | |
| --- | --- | --- | --- | --- |
|  | 2 | 3 | 4 | 5 |
| Silane mixture (mol %) | | | | |
| MeSiH$_3$ | 52.9 | 38.6 | 22.5 | — |
| MeSiH$_2$Cl | — | — | — | 50.0 |
| Me$_2$SiCl$_2$ | 47.1 | 61.4 | 77.5 | 50.0 |
| Catalyst temperature (°C.) | 100 | 100 | 100 | 80 |
| Absolute pressure (bar) | 1 | 1 | 1 | 1 |
| Dwell time (sec) | 61 | 42 | 51 | 60 |
| Product composition (mol %) | | | | |
| MeSiH$_3$ | 27.3 | 4.3 | 3.0 | 7.2 |
| MeSiH$_2$Cl | 19.5 | 23.2 | 10.0 | 23.3 |
| MeSiHCl$_2$ | 6.0 | 10.4 | 9.1 | 18.5 |
| MeSiCl$_3$ | 0.1 | 0.7 | 0.5 | 1.0 |
| Me$_2$SiH$_2$ | 2.5 | 2.8 | 1.3 | 0.4 |
| Me$_2$SiHCl | 27.5 | 34.6 | 28.5 | 13.4 |
| Me$_2$SiCl$_2$ | 17.1 | 23.9 | 47.7 | 36.2 |

Brief Description of the Drawings

The drawings are described in Examples 6 and 7 below.

Example 6 (See FIG. 1)

In a V4A steel pilot plant 1, the essential parts of which comprised an adjustable metering pump, a vaporizer, a packed column having a total length of 2.5 m and an internal diameter of 50 mm, a column head provided with a condenser, a distillation vessel of 5 liter capacity and a device for keeping the pressure constant and emptying the bottom, 1000 g/hour of methyldichlorosilane A, which was vaporized continuously in a vaporizer, were fed from a storage vessel, by means of a metering pump, under an absolute pressure of 6 bar into the lower section of the column.

The methyldichlorosilane preheated to 95° C. which enters the column filled with catalyst, the preparation of which has been described in Example 1, disproportionated, with the resulting reaction mixture separating at the same time. The higher-boiling methyltrichlorosilane B formed collected in the bottom, from where it was discharged in an amount of 870 g/hour into a storage vessel.

The low-boiling compounds passed up the column, with further reaction. The temperatures in the column were 135° C. at the bottom and 10° C. at the top. The vapor mixture C formed was removed at the top of the column and passed, together with 1500 g/hour of dimethyldichlorosilane D, under atmospheric pressure, through tube 2 which was 20 cm in diameter and 2 m long and was thermostatically controlled at 100° C. and filled with catalyst, the preparation of which has been described in Example 1. The gaseous reaction product was condensed by means of a condenser and introduced under atmospheric pressure into the center of a rectification column 3, which corresponds to the first column in respect to the dimensions but was filled with V4A metal helices 5 mm in diameter. The low-boiling compounds methylsilane, dimethylsilane and methylchlorosilane E were withdrawn at the top of the column and fed to first reaction column 1. About 1630 g/hour of a silane mixture F of the following composition:
35% by weight of dimethylchlorosilane,
44% by weight of dimethyldichlorosilane,
19% by weight of methyldichlorosilane and
2% by weight of methyltrichlorosilane
were withdrawn continuously from the bottom.

The mixture was then distilled to separate the silanes.

Figure 1:
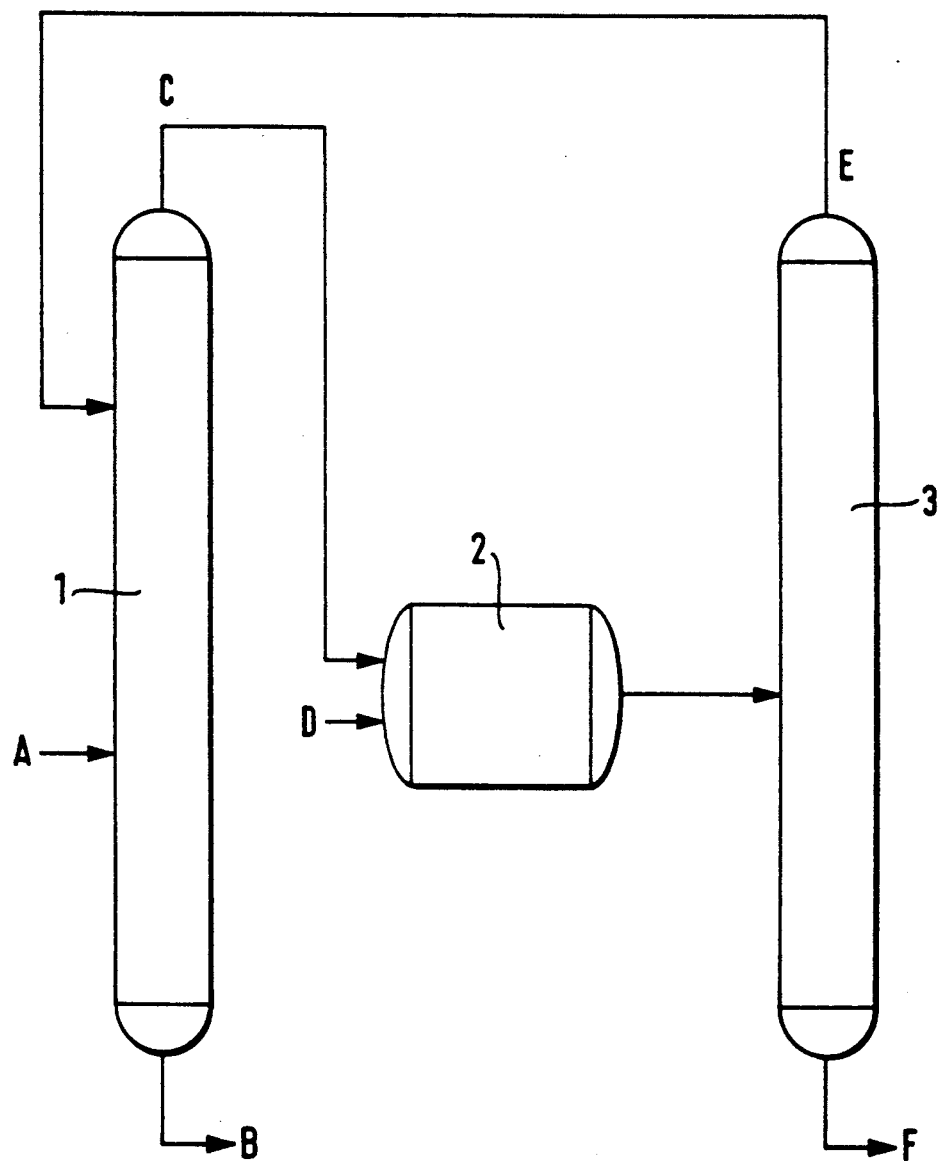
Figure 2:
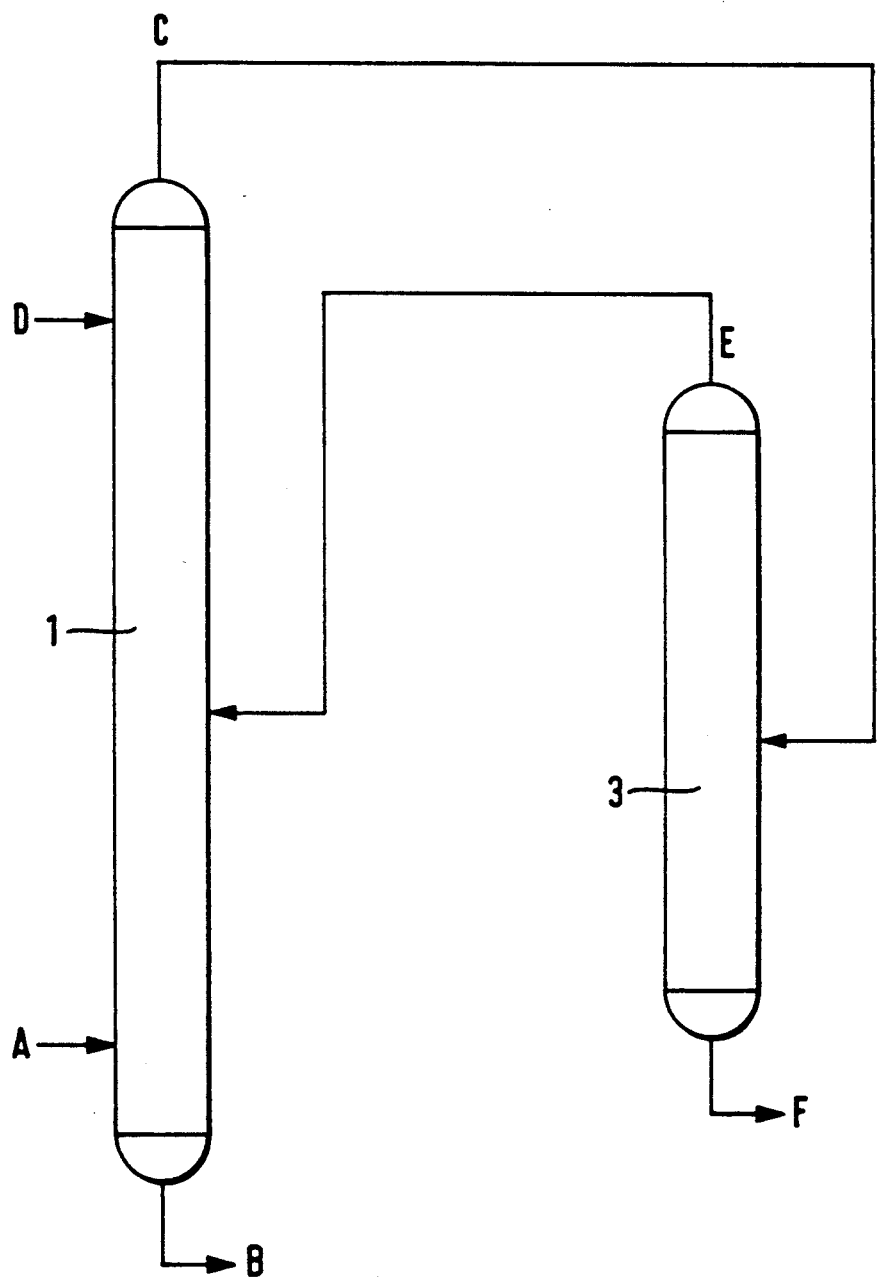

Example 7 (See FIG. 2)

The lower half of the column construction in packed column 1, which has a total length of 4.0 m and an internal diameter of 50 mm, corresponds to the reaction column described in Example 6. The total length of the column was filled with catalyst, the preparation of which was described in Example 1. Metering of methyldichlorosilane A and removal of the bottom product B (1100 g/hour composed of 80% by weight of methyltrichlorosilane and 20% by weight of dimethyldichlorosilane) were carried out as described in Example 6. The absolute pressure was 4 bar and the bottom temperature 120° C. The upper half of the column was kept at 100° C. by ancillary heaters and 1000 g/hour of dimethyldichlorosilane C heated to 100° C. were fed into this region. The low-boiling compounds methylsilane and methylchlorosilane which rise upwards in the column as a result of the disproportionation of the methyldichlorosilane react in the upper heated zone with the dimethyldichlorosilane C fed into this zone. The reaction products D were condensed at the top the distillation unit. As described in Example 6, the low-boiling of the column (temperature 80° C.) by means of cooling and left compounds E were separated in the rectification column 3 and recycled into the pressure distillation unit 1. About 900 g/hour of a silane mixture F, which contained 64% by weight of dimethylchlorosilane (boiling point 35° C.; yield 78%, with respect to dimethyldichlorosilane employed) and 34% by weight of methyldichlorosilane (boiling point 41° C.), were withdrawn continuously from the bottom of the column 2. This mixture was separated in a downstream rectification column.

What is claimed is:

1. A process for preparing dimethylchlorosilane by the redistribution reaction which comprises reacting a dimethyldichlorosilane with at least one silane having Si-bonded methyl groups, hydrogen atoms and/or chlorine atoms in the presence of a catalyst, in which the silane is a methylchlorosilane and/or a methylsilane and the catalyst is a support which is insoluble in the reaction medium and NR$_2$R$^1$ groups or $\ominus$X$\oplus$NR$_3$R$^1$ groups are covalently bonded thereto, where R represents a hydrogen atom or a monovalent hydrocarbon radical having from 1 to 20 carbon atoms per radical, or two R radicals together represent a divalent hydrocarbon radical having from 4 to 11 carbon atoms, which may optionally be interrupted by a hetero atom, R$^1$ represents a divalent hydrocarbon radical having from 1 to 20 carbon atoms per radical and X$\ominus$ represents a chloride ion, bromide ion or iodide ion.

2. The process of claim 1, wherein the methylchlorosilane and/or methylsilane are products obtained from the disproportionation of methyldichlorosilane in the presence of a support which is insoluble in the reaction medium and to which NR$_2$R$^1$ groups or $\ominus$X$\oplus$NR$_3$R$^1$ groups are covalently bonded, where R represents a hydrogen atom or a monovalent hydrocarbon radical having from 1 to 20 carbon atoms per radical, or two R radicals together represent a divalent hydrocarbon radical having from 4 to 11 carbon atoms, which may optionally be interrupted by a hetero atom, $R^1$ represents a divalent hydrocarbon radical having from 1 to 20 carbon atoms per radical and $X^\ominus$ represents a chloride ion, bromide ion or iodide ion.

* * * * *